(12) United States Patent
Kukharev

(10) Patent No.: US 11,262,379 B2
(45) Date of Patent: Mar. 1, 2022

(54) TREATMENT OF LIVING ORGANISMS BASED ON GRAVITATIONAL RESONANCES AND KUKHAREV REGION DATA

(71) Applicant: Vadim Kukharev, Moscow (RU)

(72) Inventor: Vadim Kukharev, Moscow (RU)

( * ) Notice: Subject to any disclaimer, the term of this patent is extended or adjusted under 35 U.S.C. 154(b) by 0 days.

(21) Appl. No.: 17/146,832

(22) Filed: Jan. 12, 2021

(65) Prior Publication Data
US 2022/0026463 A1 Jan. 27, 2022

Related U.S. Application Data

(63) Continuation-in-part of application No. 16/991,624, filed on Aug. 12, 2020.

(60) Provisional application No. 63/054,923, filed on Jul. 22, 2020.

(51) Int. Cl.
*G01Q 30/14* (2010.01)
*A61K 41/00* (2020.01)
*G01Q 60/42* (2010.01)
*B82Y 35/00* (2011.01)

(52) U.S. Cl.
CPC .............. *G01Q 30/14* (2013.01); *A61K 41/00* (2013.01); *G01Q 60/42* (2013.01); *B82Y 35/00* (2013.01)

(58) Field of Classification Search
CPC ........ G01Q 30/14; G01Q 60/42; A61K 41/00; B82Y 35/00

USPC ............................................ 250/492.1, 492.3
See application file for complete search history.

(56) References Cited

U.S. PATENT DOCUMENTS

| | | | |
|---|---|---|---|
| 2003/0028070 A1* | 2/2003 | Jacobson | A61N 2/02 600/9 |
| 2013/0267003 A1* | 10/2013 | Goodwin | C12M 35/04 435/173.8 |
| 2019/0056303 A1* | 2/2019 | Bahl | G01N 15/1459 |
| 2019/0151192 A1* | 5/2019 | Yamashita | A61N 7/00 |
| 2021/0196921 A1* | 7/2021 | Lin | A61M 21/02 |

\* cited by examiner

*Primary Examiner* — Nicole M Ippolito
(74) *Attorney, Agent, or Firm* — Nadya Reingand; Yan Hankin

(57) ABSTRACT

All fluids, when placed within a Kukharev region at a moment of gravitational resonance, form vibrations of different frequencies within themselves. If, at the same moments of gravitational resonance, forced oscillations of the same frequency are provided as a treatment on a living organism, a double resonance is formed within the fluid, and a sharp increase in the amplitude of oscillations within the fluid formed as a result of the double resonance in turn causes the destruction of the fluid. The method is determined utilizing Kukharev region data on the particular fluid desired to be destroyed or otherwise removed from the living organism. By further fine-tuning the forced oscillation (i.e., the directed radiation), the natural oscillations of the base fluid can be further adjusted to modify the fluid's properties.

20 Claims, 10 Drawing Sheets

US 11,262,379 B2

TREATMENT OF LIVING ORGANISMS BASED ON GRAVITATIONAL RESONANCES AND KUKHAREV REGION DATA

CROSS-REFERENCE TO RELATED APPLICATIONS

This patent application is a Continuation-in-Part of U.S. patent application Ser. No. 16/991,624, filed Aug. 12, 2020, which claims priority to U.S. Provisional application 63/054,923 filed Jul. 22, 2020, all of which are incorporated herein by reference in its entirety.

FIELD OF THE INVENTION

The present invention relates to the field of treatment of living organisms containing varying types of fluids, particularly the treatment of organisms based on data on the moments of gravitational resonance, Kukharev regions, and the impact of said moments on said fluids.

BACKGROUND OF THE INVENTION

Current medical technology does not utilize Kukharev region data, according to the present invention or the present family of patent applications. The present invention provides solutions in the form of non-invasive and non-contact treatment methods against harmful fluids within organisms and within the environment, based on Kukharev region data, as described in parent patent applications within this patent application family and hereinbelow. Acoustic and/or electric natural vibrations of different cells within the human body (especially in the range of 0-50 Hertz) have been recorded in laboratories, but their usefulness and application, as described herein, has not been realized until now.

In addition, currently existing experimental power plants utilizing the energy from lightning are experiencing problems, as exact lightning strike locations are difficult to predict. The present invention provides, among other benefits, the opportunity for providing targeted assistance to such power plants. The present invention provides the ability to understand how to descend the electrical potential from a Kukharev region to the surface of the Earth.

SUMMARY OF THE INVENTION

Kukharev regions will arise in all fluids at moments of gravitational resonance in corresponding locations due to the interference of gravitational waves from several sources. Kukharev regions are areas where fluctuations arise. For example, if the fluid consists of charged particles, then electromagnetic oscillations arise in the Kukharev region, as described herein. If, for example, the fluid consists of air, then acoustic oscillations arise. In general, the reason for the oscillations is the change of gravitational potentials at particular points under the influence of the interference of gravitational waves from several sources. For example, within the human brain, a set of fluids (or a fluid system) exists, where, for example, brain rhythms occur. Such rhythms comprise oscillations, the frequency of which is from about 1 to about 40 Hertz (usually, 8 types of different brain rhythms are distinguished at certain frequencies). Gravitational tide oscillations occurring within such fluids may be determined and further utilized in treating individuals with unwanted fluids inside the brain.

At the moment of gravitational resonance, Kukharev regions appear in all fluids. In this case, gravitational resonances are considered identical for the Sun-Earth-Moon system, for the atoms of the water molecule, as for any other gravitational system of bodies. Including in many different fluids that are inside a person, in the oceans, air, soil, artificial materials created by man. All fluids in the Kukharev regions create vibrations of different frequencies and vibrate. If, at the moments of gravitational resonance, forced oscillations of the same frequency as in the Kukharev region are provided, i.e., a double resonance is formed, then a sharp increase in the amplitude of oscillations in the fluid formed as a result of the double resonance causes the destruction of potentially any fluid, as determined utilizing Kukharev region data. By further fine-tuning the forced oscillation (i.e. radiation), the natural oscillations of the base fluid can be adjusted via a modification of the fluid's properties via the fine-tuned radiation.

BRIEF DESCRIPTION OF THE DRAWINGS

The present invention will now be discussed in further detail below with reference to the accompanying Drawings, in which the following Figures are presented.

DETAILED DESCRIPTION OF PREFERRED EMBODIMENTS

The general law of the connection between gravity and electromagnetism can be expressed as follows: Changes in gravitational potential as a result of the resonance of gravitational tides cause changes in electromagnetic potential.

This law can be written as follows:

$$\Delta A = F(\Delta \varphi)$$

Gravitational potential is a scalar function of coordinates and time, sufficient for a complete description of the gravitational field in classical mechanics. Has the dimension of the square of the speed, usually denoted by the letter $\varphi$. Electromagnetic potential usually means the four-dimensional potential of the electromagnetic field, which is a 4-vector (1-shape) indicated by the letter A. The delta symbol indicates a change. The form of the function F depends on many quantities, primarily on the frequency of gravitational waves. In practice, it is much easier to directly measure the specific values of the change in the electromagnetic potential in the Kukharev regions (in the stratopause and others) than to make accurate arithmetic calculations, which are complicated by the lack of accurate data on the parameters (amplitude, frequency) of gravitational waves emanating from the Earth, the Moon, the Sun. But the frequencies and other parameters of gravitational waves from the Earth, the Sun and the Moon have not yet been measured due to the poor accuracy of the accelerometers. That is why it is easier to measure the resonances of gravitational waves (where there is more energy) and their consequences in the Kukharev regions.

Figure 1:
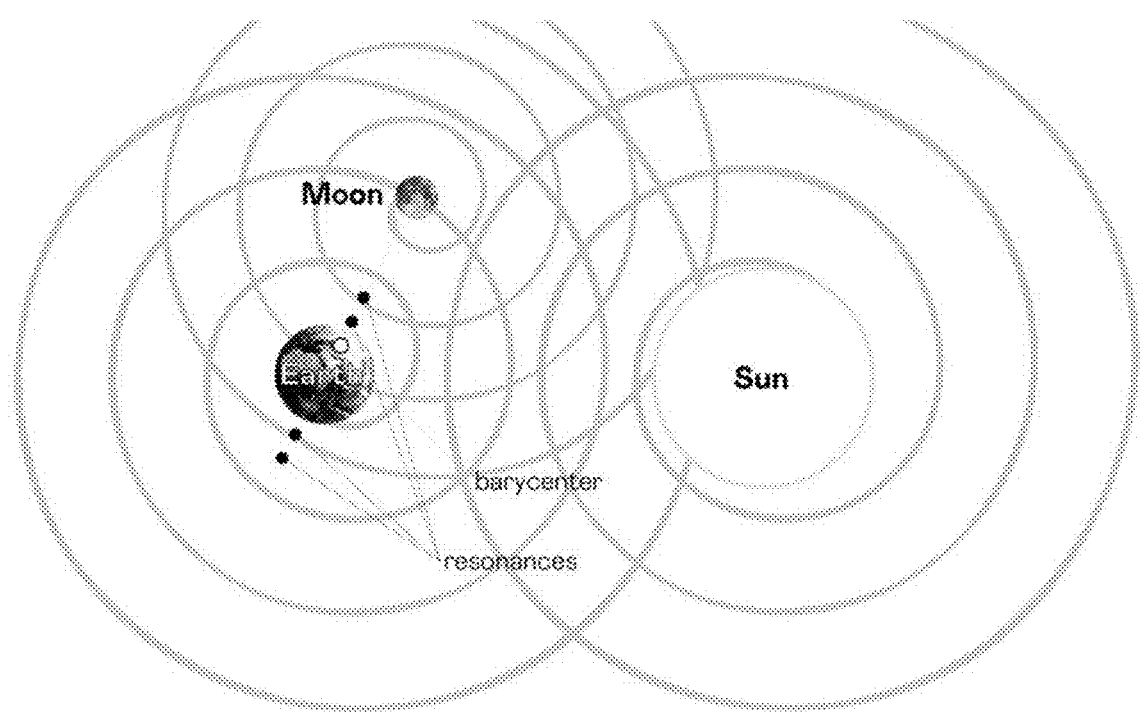
FIG. 1—Gravitational waves in the Earth-Moon-Sun system. Not all resonance points are shown in this figure; only the points most relevant for aircraft are indicated.

For rigorous analytical expressions of discovering changes in electromagnetic potential as a result of gravitational resonances in Kukharev regions, it is necessary to use a multidimensional Ricci tensor and a Calabi-Yau manifold, as well as to clearly understand the frequencies and other parameters of the gravitational waves. For practical purposes, the intersection of four normalized curves in time (Moon phase, Moon-Earth distance, depth of baricentre, distance to baricentre), introduced earlier, can be used to find appearances of Kukharev regions, as can an understanding of temperature changes that occur as a result of changes in electromagnetic potential and the appearance of electromagnetic waves. FIG. 1 shows an example of a minimal amount of the strongest resonances with the Moon (at the level of the stratopause and higher, 120 km above the Earth's surface, where temperature fluctuations and flyby anomalies exist). Gravitational tides from the Sun are also a part of the resonance with the tides from the Moon. It is extremely difficult to visualize in 2-dimensions the different varieties of gravitational tide resonances in the Earth's crust from the Sun, Moon, and mantle tides from changes in the position of the Earth-Moon system barycenter.

Figure 2:
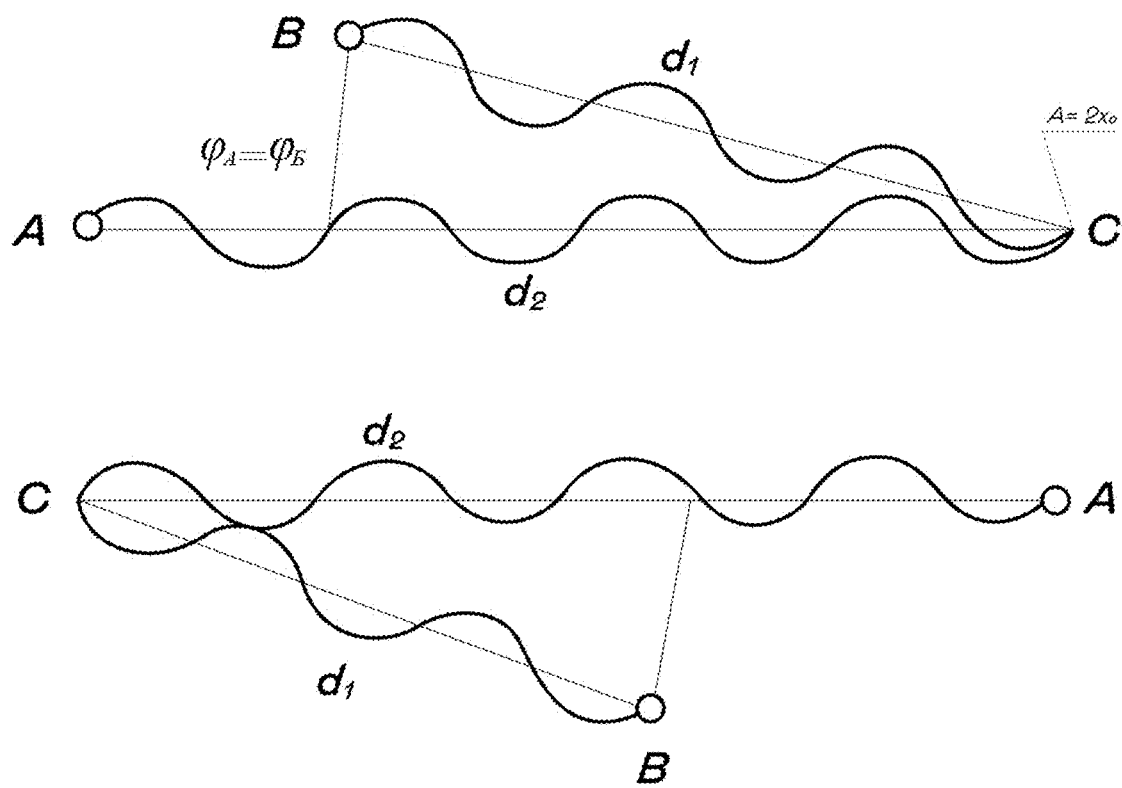
FIG. 2—Simplified diagram of the interference of gravitational waves (the top is the maximum, the bottom is the minimum).

FIG. 2 shows a simplified diagram of the interference of gravitational waves (the top is the maximum, the bottom is the minimum), but then in each tide from each body it is necessary to select a set of these waves, leave the most necessary and visual for us and work with them. To put it simply, the amplitude of oscillations, the resonance energy will be maximum for a specific point in space, if the difference in the paths of the two waves exciting oscillations at this point is equal to an integer number of wavelengths. In this case, it is necessary to calculate the energy of various types of resonances that arise at the 'intersection' of various types of gravitating factors known to us. That is, in reality, in practice, taking into account the weakness of modern methods for detecting gravitational waves and the minimality of information about their frequencies and amplitudes, for the practical use of Kukharev regions it is easier to use the intersections of 4 normalized curves in time (Moon Phase, Distance of the Moon-Earth, Depth of the barycenter, distance to barycenter), which were given earlier.

Figure 3:
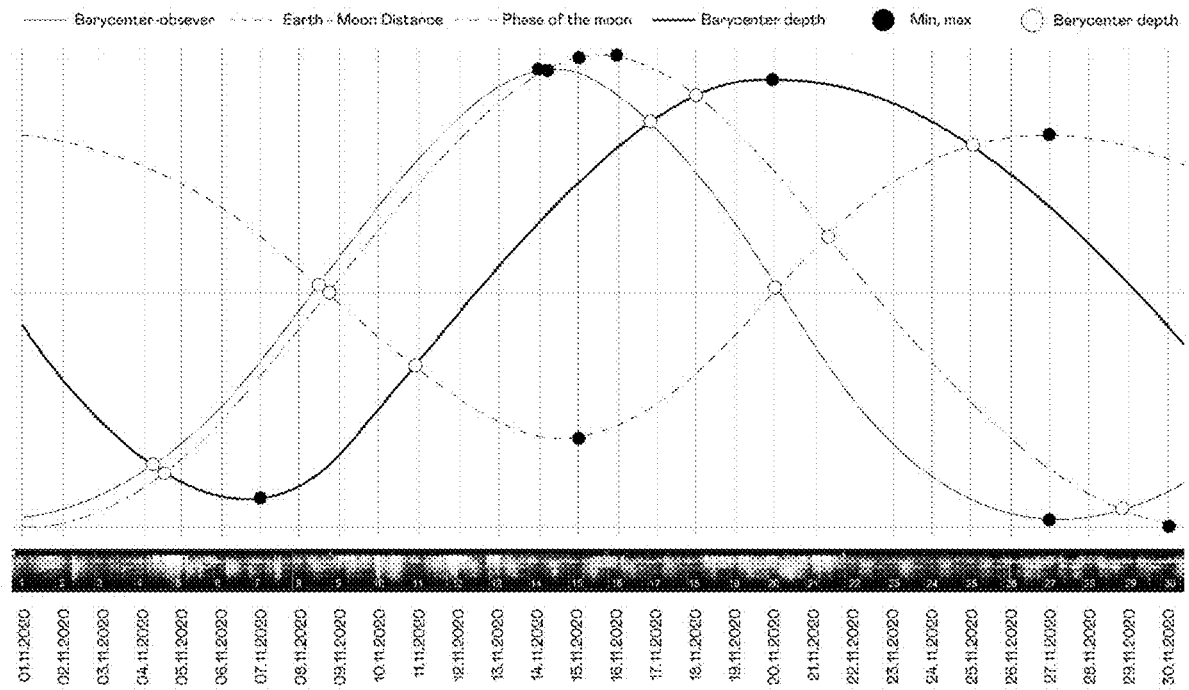
FIG. 3—Correlation between the change in the amplitude of the Schumann resonance and the moments of gravitational resonance (Lat. 56° 29.0808' 0" N, Lon. 84° 56.8918' 0" E, November, 2020).
Figure 4:
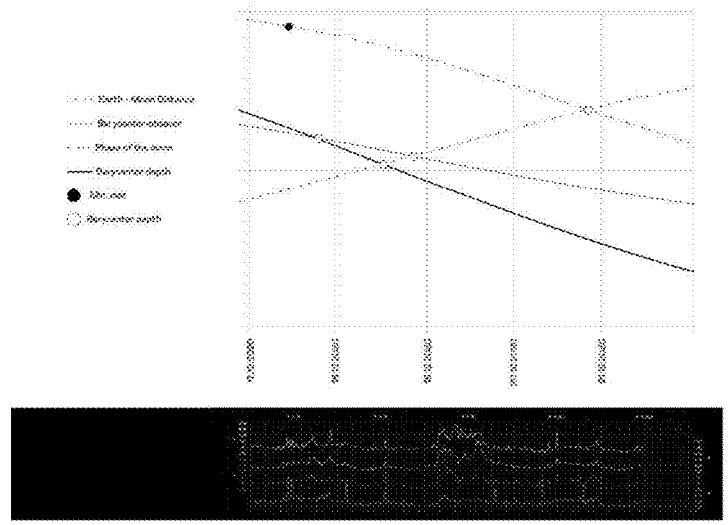
FIG. 4—A detailed view of the relationship between the moment of gravitational resonance, which creates the Kukharev regions in fluids, and the growth of the energy of the Schumann wave (which comes from the fluid), December 2020, Lat. 56° 29.0808' 0" N, Lon. 84° 56.8918' 0" E.

FIGS. 3 and 4 show in practice that at the moments of gravitational resonance, Kukharev regions arise, in which Schumann waves originate. One can see the correlation between gravitational resonance and a sharp increase in the amplitude (and energy) of Schumann waves. The physics of this process boils down to the fact that a change in the gravitational potential causes oscillations of various types of particles, changing the electromagnetic potential. In practice, it is additionally necessary to take into account the data on solar activity for the same time, taking into account the solar wind speed from 300 to 1200 km s, it is possible to delay the formation of the density of ionized particles in the stratopause and generate standing Schumann waves in comparison with solar flares from 1 to 3 days. The main (most intense in energy) Kukharev regions are steadily associated with the resonances of 14 daytime gravitational tides.

Interference is the interaction of wave processes close in frequency and phase, hence the impossibility of instantaneous transfer of energy from one wave to another. The rate at which interference occurs according to the current data is proportional to the frequency of the wave. With the interference of gravitational 14-day tides, the frequency is very low, so the process of interference of these waves lasts from several hours to a day (we already know this in practice, FIG. 4). Therefore, it is rather difficult to predict the point at which the amplitude of the interference/tidal resonance/will reach its maximum. Hence, it is clear why, for example, the energy in the Kukharev region in the part of the stratopause is registered in the form of a cloud (one can imagine a large sphere), and not a narrow, clear region.

Figure 5:
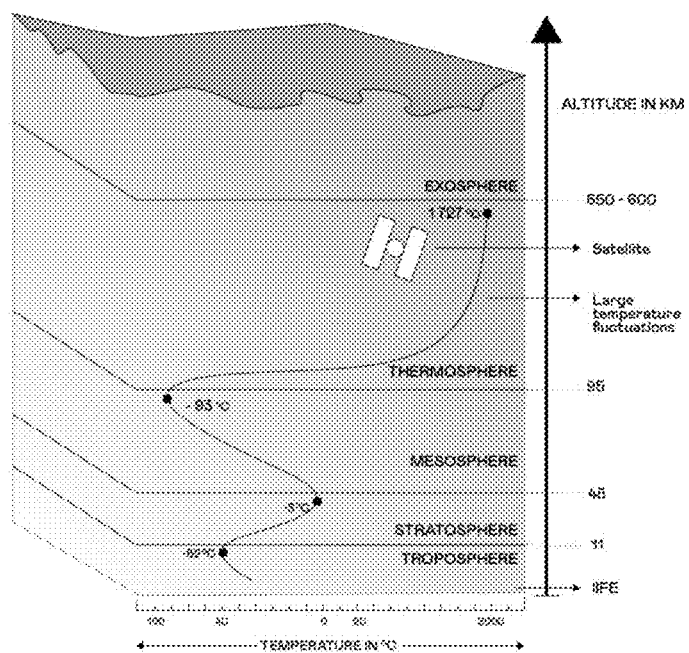
FIG. 5—Temperature fluctuations with altitude change.
Figure 6:
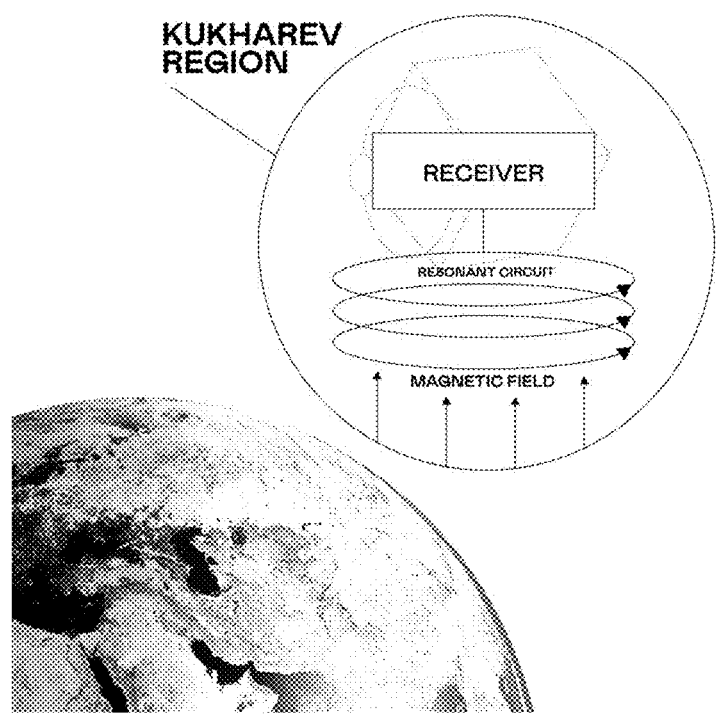
FIG. 6—General schematic diagram of the collection of electromagnetic energy in the Kukharev region.
Figure 7:
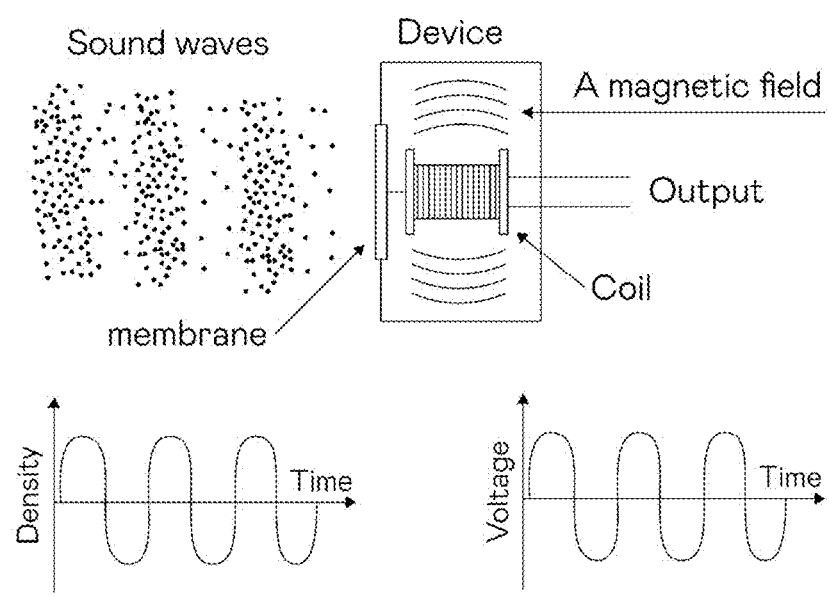
FIG. 7—General schematic diagram of the collection of sound energy in the Kukharev region and its conversion into electricity.

From a practical point of view for aircraft, there are two attractive areas (FIG. 5)—(1) the stratopause region (the height of the stratopause constantly changes from 45 to 55 km from the Earth's surface, the Moon periodically "raises" the stratopause), and (2) areas above 120 km in altitude from the Earth's surface (where temperature anomalies are visible). Both of these areas, due to the frequently occurring areas of Kukharev, contain a lot of temperature anomalies. Temperature anomalies are caused precisely by a change in the gravitational potential, which creates various vibrations (acoustic, electromagnetic).

The amount of energy in the stratopause in the Kukharev regions at the moments of resonances is estimated from 1 to 100 or more watts per square meter. The specific value depends on the strength-energy of resonance, electron density, solar wind density, season, and other parameters. For example, in the summer in the Kukharev regions (above specific points) the ionization of the solar wind and the amount of energy at the moments of gravitational resonance will always increase. An example of a simplified estimate of the amount of energy in the Kukharev region is given in the main text.

Tides in the earth's crust and deeper in the mantle are the result of the gravitational influence of the Sun and Moon. Moreover, the tides from these objects are capable of resonating. In this case, the earth's crust is in different degrees of compression-extension during the passage of the resonance energy. Similar stresses in the crust and mantle arise when the depth of the barycenter of the Earth-Moon system fluctuates. That is, the Kukharev regions arise in all fluids, including underground mineral deposits (oil, gas, mercury . . . ). The natural frequencies of the Kukharev regions in fluid/mobile and compressible mineral deposits are a cheap and effective way to search for minerals.

In general, the present technology is intended for:
receiving unlimited electrical and acoustic energy in the areas of Kukharev
destruction of cancer cells
destruction of viruses
destruction of other fluids harmful to humans
rejuvenation of a person through harmonization/normalization of fluctuations in internal fluids and the destruction of old cells in a person
removal of migraine headaches during menstruation in women, normalization of menstruation
normalization of sleep
targeted destruction of unnecessary fluids in the production of new materials
getting rid of obesity (through the remote elimination of fat cells) accelerated searching for minerals
purification of water, air, soil pollution in the form of harmful bacteria, carbon dioxide and human waste, chemical waste and other waste.

All processes are based on the creation of forcing oscillations at the same frequency as the oscillations of the target fluid, which oscillates in the Kukharev region at the moments of gravitational resonance. These forcing vibrations can be created electromagnetic, sound (acoustic) or otherwise. That is, in order to destroy or reconfigure a particular fluid at the time of gravitational resonance, a double resonance in the Kukharev region is needed. For example, this can be done if, at the moment of gravitational resonance, the electromagnetic flux of the required spectrum is directed to the fluid, if the frequency of the forcing action is generated, for example, by an electromagnetic gun on the local Kukharev region. It is necessary to excite the Kukharev regions and by a forcing effect either change the fluid or destroy it (when resonance resonates, the amplitude will sharply increase, and the fluid will burst, you can see the double resonance from the well-known story when a company of soldiers walking in step over the bridge caused its destruction). For each specific case, of course, you need a precise tuning of frequencies, you need the most accurate devices for fixing them. The general fundamental physical fact for all cases is a physical phenomenon—the Kukharev region, which appears in all fluids at the moments of gravitational resonance in the Earth-Moon-Sun system and other similar ones.

Regarding accelerated searching for minerals. The proven fact that the Kukharev regions create, among other things, electromagnetic waves in the form of Schumann resonances (as well as other oscillations), allows, in practice, to dramatically accelerate the search for minerals. For this process, one needs to perform the following: 1) In the search area, calculate the moment of creating a gravitational resonance with an accuracy of the day); (2) Place the Schumann wave receiver in the search area; (3) As soon as the amplitude of the Schumann waves begins to increase, this will show the exact moment of the onset of a gravitational resonance. That is, it will show exactly the moment of true interference of gravitational waves; (4) Strong gravitational resonances last up to 12 hours; in practice, the real duration of gravitational resonances can be tracked by waiting until the time that the amplitude of the Schumann resonance decreases; (5) The entire duration of the period of gravitational resonance is the time during which sensing devices or treatment devices should be utilized (e.g., seismographs, gas analyzers, and others). It is possible, e.g., to cover a large area with just one device, or alternatively to use a plurality of devices for the same purpose.

The general universal algorithm for influencing each specific fluid:
Isolation of a specific set of harmful fluids to be destroyed in the future (cancer cells of a certain type, viruses, . . . ).
Creation of sufficient mass in the fluid (through placement in a culture medium in test tubes and other methods).
Calculation of days of gravitational resonance (at the location of the laboratory).
Measurement by high-precision instruments of the natural frequency of fluid oscillations (high-precision mini-seismographs or their analogues) at the moments of gravitational resonance (preferably 14 days, as the strongest, but acceptable at other times, but then the accuracy of the instruments will be even greater).
Calculation and modeling of safety measures at the moment of destruction of a harmful fluid (so as not to damage neighbors and/or minimize harm from a micro-explosion).
Calculation and modeling of measures to remove destroyed fluids from the body (or other environment) (for humans—primarily through natural channels within a person)
Carrying out a standard set of measures to test technology. For a specific type of human treatment for a specific type of harmful fluids—in accordance with the requirements of the FDA (testing on animals, and so on to clinical trials in humans) and other regulatory bodies. For industrial production—standard measures for testing, acceptance tests, safety measures and others.

The procedures for collecting energy in the Kukharev regions are based on the established fact of their existence, understanding of the technology for calculating places, the time of their appearance, the frequency of oscillations in them.

Practical comparisons (FIGS. 3, 4) show a clear coincidence of the maximum energy of the Schumann waves (from the Kukharev regions) with the Sun-Barycenter resonances. Resonances with the Moon in Schumann's energetics are weaker, which is understandable given that the energy of the Schumann standing wave is primarily associated with the density of solar wind particles. The resonance of gravitational tides is a trigger for the formation of standing Schumann waves. Therefore, the higher the density of the solar wind particles in the 'bag' of the stratopause, the stronger the impact that different resonances of gravitational tides have on the stratopause.

The gravitational factors resonating once every 14 days are not less than 4 times the average ordinary amount. Accordingly, the resonances of various factors occur much more often than once every 14 days. Averaging this amount over 14 days, the pumping of fluids with the energy of resonances calculably occurs at least once every 1-3 days. The inconsistency of energy being produced based on oscillations from resonant periods and non-resonant periods leads to fluctuations in the energy potential of fluids experiencing said gravitational tide resonances, as further confirmed by observations and experimentation.

Commercial aircraft and drones typically fly in the lower stratosphere in order to take advantage of greater fuel efficiency in cold air, as well as to experience less turbulence. According to the present invention, however, such aircraft/drones should avoid Kukharev regions within the lower stratosphere at least because the electromagnetic waves from resonances will in contrast heat the air there, which will also negatively affect the electronics on the aircraft.

The Kukharev regions cause, among other things, stable wind directions (jet streams on a planetary scale), also affecting the ozone layer.

The Kukharev regions may further be taken into account throughout cosmology. The Kukharev regions explain such concepts as the "flyby anomaly" (i.e., arising gravitational anomalies for spacecraft, explained by the impact from Kukharev regions), the existence of the stratopause (i.e., the layer of heated air in the stratosphere located at an altitude of 50 km, explained by frequently occurring Kukharev regions), Schumann resonances (Kukharev regions are the source of electromagnetic waves causing Schumann resonances), and sprites, elves, and/or jets, all of which are a result of the stratopause, and serving as a potential energy source due to the Kukharev regions in which they exist. In addition, the entire theory of quantum gravity may be based on/explained by the existence of Kukharev regions, e.g., the concepts of resonance and entropy. Albert Einstein's theory of relativity takes into account neither the gravitational resonances between objects within galaxies nor the existence of Kukharev regions.

The appearance of sprites, elves and jets (primarily elves) is correlated according to current data in time and space with the passage of resonances of gravitational tides (14 days) on the Earth's surface. Through their appearance, the energy-pumping aspects of the stratopause, resulting from the energy created by gravitational resonances within Kukharev regions, is visible to the naked eye.

It is further noted that sprites, elves, and jets appear at different heights but their radiation is directed at an altitude of about 50 km, i.e., directly at the altitude of the stratopause. This fact provides additional evidence of the presence of excess energy in the stratopause via the existence of Kukharev regions.

Figure 8:
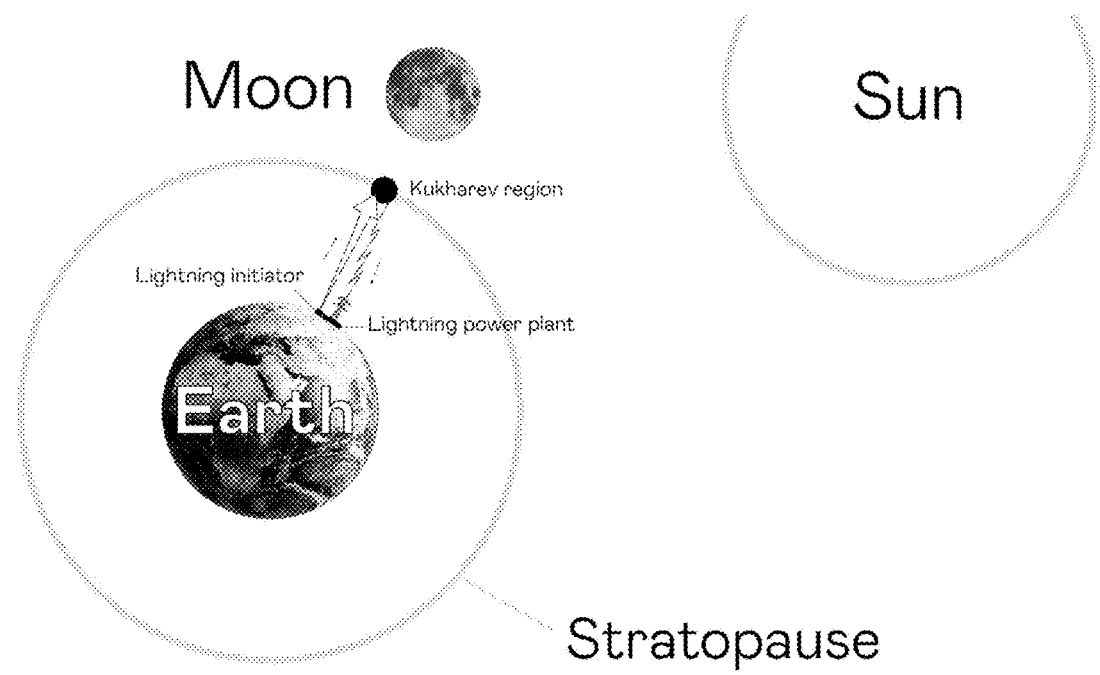
FIG. 8—Schematic diagram of the collection of electrical energy in the Kukharev regions by "descent" of energy from the stratopause (and other areas) to a ground-based lightning power plant.

To make the most of the energy within the Kukharev regions, it is necessary to transfer energy from the stratopause to the surface of the Earth (FIG. 8). It is possible to cause a discharge (i.e., a breakdown) in the form of lightning and send it to a power plant that utilizes lightning energy (i.e., a separate class of power plants from the general power-producing plant, where a current problem is the plant's inability to predict lightning for sufficient economic return). The method of collecting energy in the Kukharev region and descension of this energy to the surface of the Earth (for practical use) is as follows:

(1) Calculate the coordinates of the Kukharev region and all the moments of its passage over a thunderstorm/lightning power plant.

(2) Every period (e.g., every 2-3 days) during which the Kukharev regions form above the power plant, artificially create a plasma channel to release energy (e.g., with a laser beam). The charged particles from the Kukharev region will run downward, thus a lightning discharge will occur. Lightning, essentially being a breakdown of a capacitor in which the dielectric is air and the plates are clouds and earth, may cause the descension of the energy to the ground.

The general case for predicting lightning is provided for a land powerplant utilizing the energy from lightning strikes. The powerplant is located at some distance from many charged particles located in the Kukharev region above the powerplant. Lightning forms an electrical discharge between the powerplant means for attracting lightning and the Kukharev region. Formations of lightning may be created, e.g., by: (1) reducing the distance from the Earth's surface to the charged particles using a conductor, (2) ionizing the air within the space between the ground and the charged particles (e.g., creating a conductive channel, such as a sprite), or (3) increasing the electric potential below the charged particles.

Each of the above 3 methods is implemented in practice, as exemplified below.

(1) Reduction in distance: a) To reduce the distance from the surface of the Earth to the charged particles (of the Kukharev region), install a long, wet mast from the powerplant; b) provide a metal ball tied to a metal wire, grounding one end of the wire, and raise the ball, e.g., using a drone as high as possible, the raising leading to a decrease in the distance and thus the increased occurrence of lightning; c) by raising (i.e. launching) an aircraft with a conductive rope in a similar manner (e.g., a wire or thread), a lightning strike is triggered at known moments of gravitational resonance within Kukharev regions, d) water may also be used to induce lightning strikes, since water is a conductor (e.g., if the jet stream of water is directed upward, the distance to the charged particles will decrease and a discharge (i.e., lightning) will occur.

2. Air ionization: a) ionizing the air space with an electromagnetic wave increases the conductivity of the air (thereby decreasing the resistance of the air), and leading to a discharge, b) using ultraviolet, x-ray, laser, gamma or radioactive radiation to ionize the air, for a same result, or c) ionizing air by heating, as high-temperature gases have low resistance, which will lead to the discharge.

3. Increase in potential at the surface (i.e., below the Kukharev region): a) creating an additional charge below the charged particles (and under the powerplant) with a very sharp movement or rotation occurring at the location of the powerplant's receiving mast(s), b) increasing the potential using an electrophoretic machine, c) providing a mobile mast on a vehicle or otherwise rapidly moving platform, and as the mast interacts with air, as a result of electrification, charged particles appear on the mast, leading to an increase its electrical potential and the causation of a discharge, d) with a sufficiently size body of water, i.e., if the charge of the particles in the water has a sufficient potential, electrical induction may be provided on the surface of the water to increase the electrical potential until a discharge occurs.

It is further noted that combinations of the methods described herein may also be utilized to induce lightning discharges. Furthermore, any explosion may provoke a lightning discharge. All described and equivalent methods of lightning induction are possible for utilization by thunderstorm powerplants in order to facilitate predicting lightning based on data from the Kukharev regions at determined moments of gravitational resonance.

It is noted that collecting energy locally and descending it to the surface of the Earth are two different manners of utilizing energy. To release energy to the ground, a laser beam or an otherwise direct flow of energy is required. Alternatively, lightning powerplants are designed with the theory of receiving strikes of lightning to harvest energy. The problem, however, with such powerplants is their return on investment because of the randomness of and difficulty in predicting lightning strikes.

The present invention solves the problem of the unpredictability of lightning strikes. Kukharev regions in the stratopause, at the moments of gravitational resonance, resemble oscillations of charged particles (in volumes having a radius of about 5 km) which form an electric potential. By creating an opening (i.e., a puncture) in a lower portion of the Kukharev region, providing, similar to a sprite preceding a lightning bolt, a pathway for descending the electrical potential to the ground, e.g., utilizing a laser beam.

Essentially, the task for descending energy becomes to create a conducting channel between the Kukharev region and the Earth/ground. Such a conductive channel may be formed, e.g., with a laser beam or a rocket. Another critical factor, however, for descending energy is where to provide the energy descension. The strongest Kukharev regions arise at the height of the stratopause (50 km) every 14 days. Weaker Kukharev regions appear every 2-3 days. A short pulse of laser radiation directed at a Kukharev region will cause the formation of lightning, and the mast of any lightning powerplant should be near to the emitter providing the laser radiation). Thus, by forming a conductive channel from the Kukharev region to the Earth's surface, a descension of energy occurs from the Kukharev region to the Earth's surface, where the energy can be further harvested and utilized as a power source.

Figure 9:
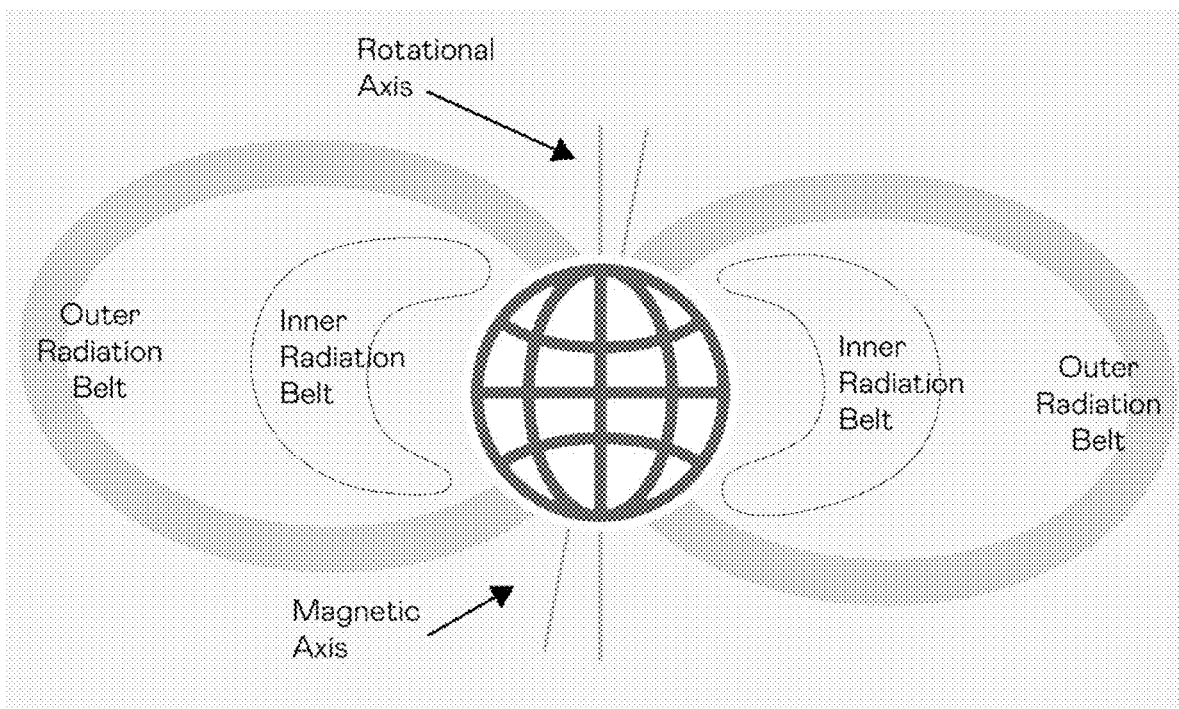
FIG. 9—Van Allen radiation belt.
Figure 10:
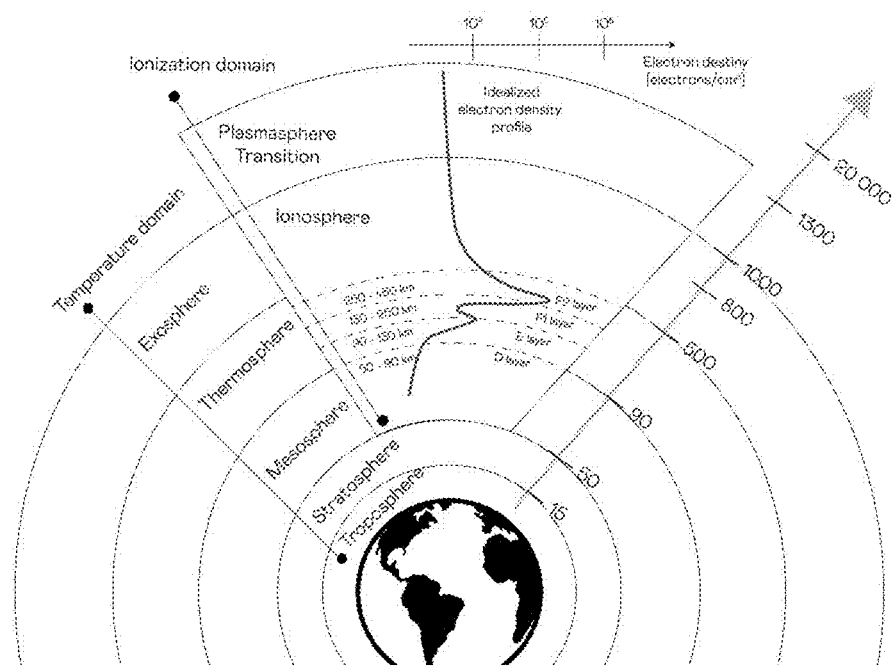
FIG. 10—Change in electron density at different altitudes.
Figure 11:
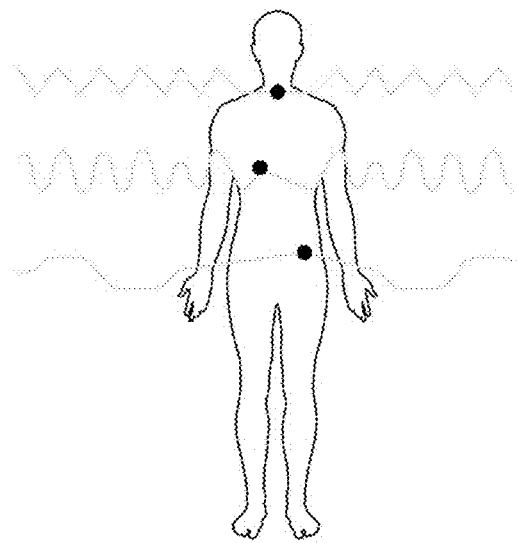
FIG. 11—The human body is like a multitude of fluids at the moment of gravitational resonance.
Figure 12:
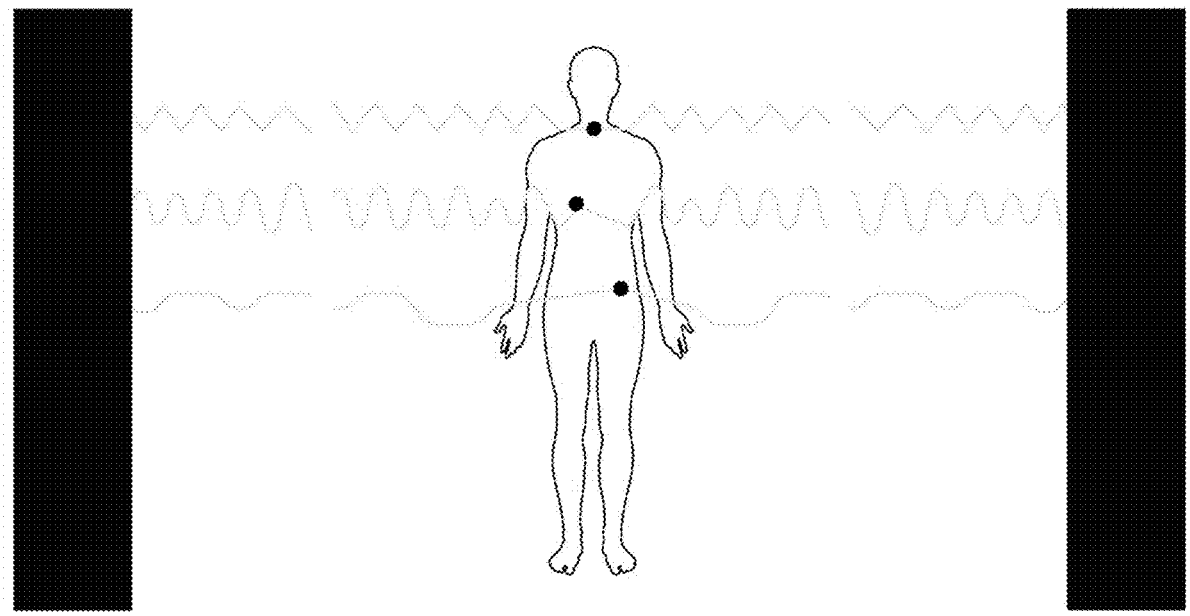
FIG. 12—Removal of unnecessary fluids for human treatment at moments of gravitational resonance by creating directional radiation of the same frequency as harmful fluids.

Kukharev regions exist both in the stratopause and above, in different parts of the planet and containing different amounts of energy. These amounts of energy depend on the density of the air, the amount of energy particles, and other constituents that are affected by gravitational resonances. For example, the Kukharev regions passing through the Van Allen radiation belts contain more high-energy electrons. Accordingly, when collecting energy from the Kukharev regions, the distribution of electron density around the planet must also be taken into account (FIG. 9).

The resonances of gravitational tides are triggers for changes within the stratosphere, the atmosphere, seas, oceans, and all fluids including those within humans. It is necessary, in the general case, to distinguish between a gravitational wave and a gravitational tide. It is the resonance of gravitational tides that changes the gravitational potential in the Kukharev regions, and a change in the gravitational potential leads to a change in the electromagnetic potential. In this case, Poincaré's theorem (through Perelman's proof) can be combined with the fact that light moves along geodesic lines along extrema, placed sensitive gravimeters, magnetometers, electric potential meters (as well as other devices) at different Lagrange points, and more accurately measure the characteristics of gravitational waves. It is only necessary to take into account and understand that at these Lagrange points (which are similar to a stratopause) Kukharev regions will appear in the same way, and at the moments of resonances of gravitational tides, it is possible to identify massive changes in electromagnetic potential. Ground stations for observing the gravitational field (in fact, any person with a sufficiently sensitive gravimeter) may also independently observe the moments of resonances of gravitational tides and utilize the energy formed within Kukharev regions according to the present invention.

It should be noted that the resonance of gravitational tides in the Earth-Moon-Sun system at the moment of its occurrence is created at once in a multitude of points in space. The rotation of the Earth, the rotation of the Moon and the Sun must also be taken into account. First of all, for practical purposes of use, it is worth paying attention to the rotation of the Earth, and the potential passage through Kukharev regions in an array of points/locations.

An exemplary simplified estimate of the amount of energy in the Kukharev region in the Earth's atmosphere can be made as follows. Calculation is performed based on an understanding of the change in air temperature under the influence of an electromagnetic wave (a simplified separate version goes further).

Average mass heat capacity of air at constant volume $C_{VT}$ in the temperature range from $t_1=-100°$ C. to $t_2=0°$ C., is as follows:

$$C_{vm-100}=0.7167 \text{ Kilojoule/kg·K};$$

$$C_{vT0}=0.7171 \text{ Kilojoule/kg·K}.$$

On Earth, the stratopause is located 50 to 55 kilometers (31-34 miles) above the Earth's surface. The atmospheric pressure there is around $\frac{1}{1000}$ of the same pressure at sea level. In practice, according to satellite data, the existence of temperature jumps in the stratopause, from 1 to 10 degrees, is known. These jumps correspond to the formation of the Kukharev regions and the electromagnetic radiation resulting from their existence. Such jumps correspond to an energy of more than 1 Watt per square meter.

The relevance and significance of the proposed invention is associated with at least the following problems under the current state of the art: Stratospheric aircraft and high-altitude platforms require a constant source of energy to remain in the air continuously. Solar panels cannot fulfill this requirement to a sufficient degree. Dust, soot, pollen, and other particles reduce the efficiency of solar panels. Solar panels from satellites and balloons require significant investment in cooling systems. Solar panels also require toxic substances for their production. The present invention provides a solution for stratospheric aircraft and high-rise platforms experiencing issues in any part of the design or implementation process, resulting from the dependence on conventional solar-based energy. The following table (Table 1) provides categorical comparisons of conventional solar-based energy and the utilizing energy accumulating in the Kukharev regions of the present invention.

TABLE 1

Comparison of energy production technologies for high-rise platforms

| | CONVENTIONAL SOLAR ENERGY FOR HIGH-ALTITUDE PLATFORMS | KUKHAREV REGIONS |
|---|---|---|
| Effective constant average energy (for consumption). Real average annual output. Average rating, including nighttime. Watts/m2 of receiving device. | 40-70 | Approx. 1 to 100 watts per square meter (the exact value is clarified after experimentation; the power of the Kukharev regions depends on a number of parameters, including the level of electron density at the time of gravitational resonance). |

TABLE 1-continued

Comparison of energy production technologies for high-rise platforms

| | CONVENTIONAL SOLAR ENERGY FOR HIGH-ALTITUDE PLATFORMS | KUKHAREV REGIONS |
|---|---|---|
| Weight (kg/m2) | 10-20 | Less than 5 |
| Problems | Decreased efficiency from dust, grime, pollen and other particulates accumulating on solar panels. Cooling systems are expensive. Use of toxic substances in photocells. Constant orientation to the Sun. | None (gravitational waves are constant everywhere) |
| Cost | More than $2 per watt | Less than $1 per watt |
| Utilize batteries to equalize the flow of electricity for consumers | Yes | Yes |

The following evidence of the existence of Kukharev Regions has been confirmed:

1) A clear correlation exists between moments of gravitational resonance in the Earth-Moon-Sun system and changes in the amplitude of Schuman resonances.

2) A near 100% correlation exists between moments of gravitational resonance in the Earth-Moon-Sun system and temperature and pressure changes in the stratopause.

3) A correlation exists between moments of gravitational resonance in the Earth-Moon-Sun system and the appearance of sprites and elves.

4) A correlation exists between moments of gravitational resonance in the Earth-Moon-Sun system and the appearance of flyby anomalies.

The following table (Table 2) presents estimated values of the potential attributes associated with various parameters of energy collected from Kukharev regions, according to the present invention.

TABLE 2

Approximate parameters of a ground-based lightning power plant utilizing energy accumulated in Kukharev regions.

| Parameter | Estimated value |
|---|---|
| Output Power | More than 10 kilowatt per hour |
| Possible installation locations | Anywhere gravitational forces exist. Installable in rows, one after the other, with a distance, e.g., of several kilometers between each sensor. |
| Cost of power plant | Less than $1 million |
| Raw materials required | None |
| Harm to the environment | None |

It is further helpful to look at the temperature fluctuations in the atmospheres of other planets. If a planet has no satellites, there is no gravitational resonance, and therefore, no Kukharev regions. On a similar planet, temperature anomalies also will not be found (i.e., the cause of a stratopause). The figures herein illustrate how many satellites each of the planets of our solar system has. If a planet has several satellites with significant mass, then gravitational resonances will differ from the characteristic features of resonances of gravitational tides in the Earth-Moon-Sun system.

To summarize: Kukharev regions appear in all fluids at varying moments of gravitational resonance, and they can be observed throughout the universe.

Kukharev regions create the following: Schumann resonances in the Earth's ionosphere, stratopauses on all planets with satellites, other temperature and other anomalies, local changes in the gravity field and flight performance anomalies, and symmetry and quantum anomalies in the microworld.

It is further noted that the Kukharev regions, located both in the stratopause and at higher altitudes in different areas of a planet, contain different amounts of energy. These amounts of energy depend on the density of the air, the amount of energy particles, and other constituents that impacted by gravitational resonances. For example, the Kukharev regions passing through the Van Allen radiation belts contain more high-energy electrons. Accordingly, when collecting energy from the Kukharev regions, it is necessary to take into account the distribution of electron density around the planet. It should also be noted that plasmoids, sometimes observed by astronauts, also form in the Kukharev regions (i.e., high electron density).

Utilization of the Kukharev Region Data in Treating Living Organisms.

Figure 13:
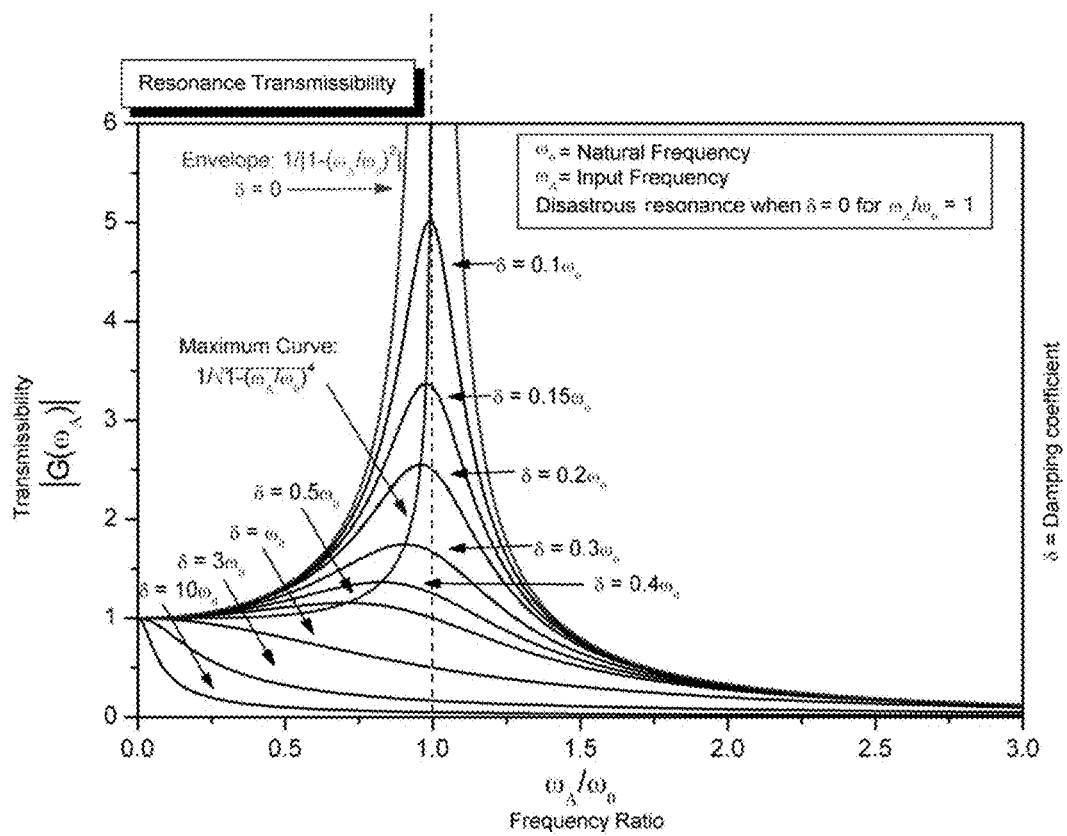
FIG. 13—A sharp increase in resonance when frequencies coincide.

Further below is a description of the utilization of the relationship between gravity and electromagnetism in the Kukharev regions, particularly for the treatment of or other benefit to living organisms. Since the Kukharev regions arise due to the interference of gravitational waves in all fluids, the resonance effect (FIG. 13) may be utilized to destroy and regulate all undesired fluids.

Old age results in the accumulation of errors in human cells and the general accumulation of unnecessary and old cells in the human body. Cells can be returned to a younger state if they are placed in a younger environment—e.g., cultivated in the blood serum of a young animal, or if perhaps the circulatory systems of young and old individuals are somehow connected. In order to prolong human life, the current technology proposes a constant controlled apoptosis (i.e., a regulated process of cell death). By understanding the exact vibration frequencies of any unwanted cells on the day of a gravitational resonance, and then providing a counter frequency based on this understanding, the present invention provides a method through which to constantly destroy unwanted cells/fluids by creating vibrations of the same (or an equal but opposite) frequency on the same resonance day(s). Each such group of cells/fluids, at their respective moments of gravitational resonance, has its own frequency. The present inventive technology of identifying resonance days and locations of Kukharev regions has a significantly greater accuracy than many of today's drugs and/or therapies, which further tend to attack an entire cluster of cells without truly differentiating between healthy and diseased/undesired cells/fluids.

In the non-limiting example of coronary heart disease, at some point, the atherosclerotic plaque tears and a thrombus forms with the development of myocardial infarction and ventricular arrhythmia. The man falls and dies. but atherosclerotic plaque is a specific fluid. At the moments of gravitational resonance, the Kukharev region of the plaque vibrates at a specific frequency. If a directional vibration of the same frequency if provided, the atherosclerotic plaque will be destroyed under the double resonance, thereby prolonging the patient's life.

The following factors regarding such treatment are also relevant:

(1) It is necessary to avoid side-effects of any created vibrations on desired cells/fluids (e.g., their destruction as a side effect of creating resonant vibrations). For this reason, it is necessary to know, as accurately as possible, all frequencies of all relevant fluids located within an organism being treated by this method. At minimum, an accuracy to one-thousandth of a frequency unit is required.

(2) If the unwanted fluid in the organism is mixed with a desired fluid (i.e., they are inseparable), then it is necessary to work with the mixture as a single entity (if medically appropriate) and with the general frequency of the oscillations of the entire mixture at the moments of gravitational resonance.

(3) At the boundaries of each allocated fluid reservoir, the fluid is less dense/thick, and therefore the frequency of the standing wave in that area is higher than in more central areas of the fluid.

(4) The natural vibrations of each fluid are determined by its viscosity and the geometric parameters of the fluid object.

In the case of this application of the present invention, the technology of rejuvenating a living organism (human or other creature) implies the requirement of constant removal of old cells. The concepts of "old" and "young" cells will depend on the chronological age of a particular patient. For each patient, it is recommended to draw a complete map of the vibrations of all his/her cell groups at the periods of gravitational resonance. The complete map will be a marker map of the patient's biological age. Such maps may be identical for all people in the same age group. At the same time, after the mapping out of the patient, the patient's illnesses will be more visible and detectable. Therefore, the present invention also provides for a system for generally diagnosing an organism.

It is generally known that there are many cells in the human body that remain "young" up to the conventional age of old age (60-90 years). This technology implies precisely the constant maintenance of the maximum number of young cells, consistently, carefully removing old cells in many sessions (so as not to harm a person and to carry out rejuvenation not instantly, but for some time).

There are proteins within humans (such as 15-PGDH), the excess of which is associated with aging. The present inventive technology allows one to accurately remove unnecessary fluids from the human body, and other damaged, harmful proteins. One can also remove excess reactive oxygen species and free radicals, emulate diet (removing excess nutrients), and lower sugar levels. In this case, after the destruction of unnecessary cells, stem cells must constantly divide, creating new cells which then need to be stimulated.

To maximize the extension of human life, one needs to actually copy the model of rejuvenation of naked mole rats (rodent family). That is, to take statistically their system of regulation of cellular aging, that is, the ability to very accurately determine which cells it is time to get rid of and introduce it for *Homo sapiens*.

The scope of the destruction of harmful fluids also includes the targeted destruction of free radicals and unnecessary sections of mitochondrial DNA, emulation of the targeted effect of antioxidants (which are found in fruits, cocoa, green tea, etc.) to slow down cell oxidation and slow down aging.

The technology of tuning to the desired fluids in the human brain is based on point neuron stimulation, which includes a very smooth increase in the power of conjugate resonances of the resonance of the desired fluids. For example, Parkinson's disease is caused by the progressive destruction and death of neurons that produce the neurotransmitter, dopamine—primarily in the substantia nigra, as well as in other parts of the central nervous system. Insufficient dopamine production leads to an activating effect of the basal ganglia on the cerebral cortex. The treatment based on the present invention will, e.g., comprise amplitude stimulation of neurons, determination of the natural frequencies of vibration of these neurons at the moments of gravitational resonance, and careful sequential stimulation of these neurons with signals of the same frequency with a change in amplitude. Unnecessary neurons can be removed via this process.

In the body of the average adult, about 50-70 billion cells die every day as a result of apoptosis. For the average child between the ages of 8 and 14, the number of cells killed by apoptosis is in the order of 20-30 billion per day. The total mass of cells that undergo destruction during 1 year of life is equivalent to the mass of the human body. At the same time, the replacement of lost cells is provided due to proliferation—an increase in the cell population through division. The presented technology of artificial directed programmed cell death will be useful to all medicine for the treatment of oncological, autoimmune, and neurodegenerative diseases.

In addition to old cells, it is necessary to constantly remove tumors of all kinds that harm humans. The mechanism for removing such tumors is exactly the same as for all other harmful fluids.

Cellular senescence is a phenomenon that is also associated with the loss of the cell's ability to divide (Hayflick limit). Cellular aging is one of the mechanisms of aging in the body. For most human cells, the Hayflick limit is 52 divisions. The Hayflick border is associated with a reduction in the size of telomeres, sections of DNA at the ends of chromosomes. Therefore, the complete procedure for human rejuvenation should be complex (not only the removal of old cells, but also the initiation of new ones by either editing DNA or by amplitude action on telomeres)

In naked mole rats there is practically no aging at the level of the organism (aging), they are resistant to cancer, their system of cellular aging (senescence) works very actively and efficiently, destroying all "bad" cells. But the manifestation of aging at the level of the body is not a direct consequence of the aging of damaged cells. The old organism does not consist only of cells with signs of cellular aging, in it only their proportion is higher. For example, in young mice, the proportion of cells with signs of senescence is 8%, while in very old individuals this proportion increases to approximately 17%. In some organs—for example, the heart, skeletal muscles and kidneys—the proportion of cells with signs of cellular aging does not grow at all during life, although these organs themselves undoubtedly work worse with age. This means that the aging of an organism is more complex than the sum of the aging of its individual cells, and aging occurs, among other things, due to subtle disturbances in the regulation of intercellular interactions. These intercellular interactions (since everything happens in a liquid medium) are also an example of fluids in which Kukharev regions arise, which can and must be regulated.

A wealth of evidence further indicates that aging is also caused by kinks in mechanisms that are beneficial when moderately active. These are the mechanisms that contribute to aging: accumulation of reactive oxygen species, weakening of signaling along the insulin pathway, inflammation. In small doses, all this is beneficial to the body, but when these processes are abused or imbalanced, the effect is instead destructive not only for the cell itself, but for the whole organism.

The technology for removing harmful fluids is also recommended for biomarkers of aging (remove glycated proteins, so-called AGE products). AGE products accumulate over time and disrupt the functionality of cells and tissues. This is especially pronounced in the cardiovascular system, where vessels lose elasticity with age due to cross-links in collagen caused by glycation. Removing 8-oxo-2'-deoxyguanine (which increases with age) will also slow aging.

For an even more complete fight against aging, it is necessary to use the understanding that with the age of a person, his entropy increases. Entropy slows down all biological processes to the point of stopping. Entropy has a de facto inertia brake function. But this is described in more detail in another patent application related to the concept of boson-energon time (Kukharev boson, Copyright 1-4137983761 from Nov. 4, 2016).

Figure 14:
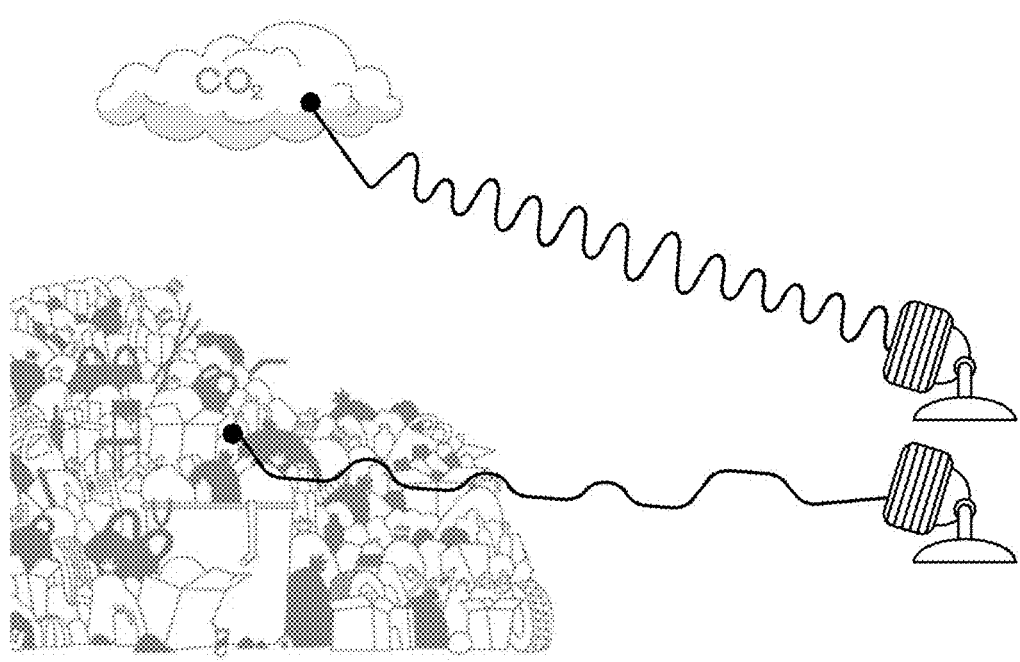
FIG. 14—Destruction of waste, harmful fluids at the moments of gravitational resonance by directed vibrations of the same frequency as in the Kukharev region of the corresponding harmful fluid.

The destruction of harmful fluids in the form of unnecessary gases (such as carbon dioxide associated with global warming), debris and other substances (FIG. 14) is also carried out by the directed creation of oscillations at the same frequency as the natural oscillations of these fluids at the moments of gravitational resonance (in the Kukharev regions).

The treatment method comprises the following steps: (1) a patient requests treatment for removal of an undesired fluid (e.g., cancer, old cells, or fat cells, generally unwanted fluids), (2) knowing the coordinates of the location of treatment location, calculating the periods/dates of the gravitational resonance (as described herein) at the treatment location, (3) knowing the natural vibration frequencies of the specific fluids at the moments of gravitational resonance, identifying the vibration frequencies at which the undesired fluid resonates during said known moments of gravitational resonance, (4) the patient receives treatment on the date(s) corresponding to the period(s) of gravitational resonance, said treatment comprising: (a) determining, using a Schumann wave receiver, an onset of a gravitational resonance when the amplitude of the Schumann wave receiver output begins to increase, (b) wherein the moment at which a decrease in the amplitude output of the Schumann wave receiver indicates the end of the gravitational resonance, (c) strong gravitational resonances (occurring typically every 14 or 28 days) last up to 12 hours, during which the treatment should occur because vibrations of various fluids are known at these times of gravitational resonance, (d) during these known times, radiation of the same frequency as the known resonant frequency of the undesired fluid is provided and directed towards the patient, (e) as the overlapping of equal frequencies occurs within the organism being treated, particular within volume(s) comprising the undesired fluid, a double resonance occurs, said double resonance breaking apart (i.e. destroying) the undesired fluid due to a sharp increase in the amplitude of the oscillations within the undesired fluid.

Neighboring cells to the undesired cells are not impacted, as other types of fluid will vibrate at different frequencies than those directed at the patient. The provider of treatment should utilize a device serving a function identical to that of a conventional ultrasound examination device, but at the same time, the device according to the present invention further operates at frequencies close to infrasound (i.e., essentially functioning also as an oscillator). For this reason, all healthy areas of the human body must also be considered prior to treatment in order to properly protect those healthy areas from any radiation provided (e.g., fluorography is performed in a similar manner).

It is further noted that it is necessary to know exactly the natural frequencies of the constituents of the organs, including both healthy and unhealthy cells, of a particular patient. The ability to properly apply the teachings of the present invention, i.e., to select the particular frequency comprising external influences in order to ensure the destructive double resonance of only the unwanted cells. It is necessary to take into account that the frequency of standing waves of varying fluids depends not only on the nature of the cell, but also on the size of a particular neoplasm (i.e., the patient should be able to otherwise determine the size of a cancerous growth in advance, from another examination, prior to receiving the treatment of the present invention). Prior to treatment, it is necessary to take into account the biophysical characteristics of the patient in order to reasonably select the frequency and time of exposure, with standards similar to those for methods for radiotherapy.

Devices utilized for the treatment of the organism, i.e., devices which create the vibrations to be directed towards the patient on day(s) of gravitational resonance, should functionally operate in a wide range of frequencies (e.g., vibrations from 0 Hz to several GHz). One or more devices may be used in combination for a single treatment. Functionalities of the device include providing the frequencies associated with infrasound and those frequencies associated with ultrasound, since most of the cells vibrate at the moments of gravitational resonance at frequencies from 0 to 100 Hertz (this corresponds to both the vibration frequencies of the first five Schumann harmonics and the vibration frequencies of oil and gas, as they are all in the same corridor). The standing wave must enter into a double resonance to destroy the unnecessary fluid.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

TABLE 3

The following table (Table 3) summarizes the various applications of Kukharev region data, as discussed in the above description.

| No | Technology direction | What is fluid? | What is the target region of Kukharev (most effective in practice) | Energy type | Method of practical use of the Kukharev regions (including impact) |
|---|---|---|---|---|---|
| 1 | Getting unlimited energy | Masses of gas and particles in the atmosphere | Energy balls are Kukharev's regions in the stratopause (usually up to 5 km in diameter) that arise at the moments of gravitational resonance, causing pressure and temperature drops. Smaller areas of Kukharev also appear in the atmosphere, but in practice they are less effective. | Electromagnetic  Sound (acoustic) | Directly at the place of origin, as a source of energy for drones, airships, balloons "Descent" of energy to the ground in the form of a lightning discharge, which will strike at the right place. Directly at the place of origin |
| | | Interplanetary plasma and solar wind particles | All points through which the resonance of gravitational tides goes, primarily the Kukharev region above 120, where temperature anomalies and flyby anomaly are recorded | Electromagnetic | Power source for satellites and spaceships |
| 2 | Medical direction: destruction of cancer cells destruction of viruses destruction of other fluids harmful to humans rejuvenation of a person through harmonization/normalization of fluctuations of internal fluids and the destruction of old cells in a person removal of migraine headaches during menstruation in women, normalization of menstruation normalization of sleep | The body of a person (or other living creature) and its constituent cells and groups of cells | All points through which the resonance of gravitational tides goes | — | Destruction of unnecessary fluids or their change by purposeful action at their own frequency and near frequencies |
| 3 | Material production | All fluids in materials production | All points through which the resonance of gravitational tides goes | — | Destruction of unnecessary fluids or their change by purposeful action at their own frequency and near frequencies |
| 4 | Environmental direction - cleaning of environmental pollution | Carbon dioxide, other harmful gases and liquids, fluids in all types of waste (including plastic) | All points through which the resonance of gravitational tides goes | — | Destruction of unnecessary fluids or their change by purposeful action at their own frequency and near frequencies |

What is claimed is:

1. A method for treating a living organism, comprising:
identifying an undesired fluid within the living organism,
determining the coordinates of a treatment location,
calculating one or more periods of a gravitational resonance occurring at the treatment location,
determining a vibration frequency of the undesired fluid within the living organism during the one or more periods of a gravitational resonance,
providing a treatment, at the treatment location, to the living organism, during the one or more periods of a gravitational resonance, the treatment comprising:
monitoring for a reception of a Schumann wave,
determining an onset of a predetermined period of a gravitational resonance, the onset occurring when a monitored Schumann wave amplitude begins to increase,
administering a radiation to the living organism during the predetermined period of a gravitational resonance, said radiation having a frequency equal to the vibration frequency of the undesired fluid during the predetermined period of a gravitational resonance,
determining a decrease in the monitored Schumann wave amplitude, said decrease indicating an end of the predetermined period of a gravitational resonance, and
concluding the treatment.

2. The method of claim 1, wherein the one or more periods of gravitational resonance occur once every 14 days.

3. The method of claim 1, wherein the one or more periods of gravitational resonance occur once every 28 days.

4. The method of claim 1, wherein the one or more periods of gravitational resonance lasts up to 12 hours.

5. The method of claim 1, wherein the radiation is administered directly toward the living organism.

6. The method of claim 1, wherein an overlapping of equal frequencies occurs within the undesired fluid, thereby forming a double resonance, said double resonance destroying the undesired fluid.

7. The method of claim 1, wherein the undesired fluid comprises old or sick cells.

8. The method of claim 1, wherein the undesired fluid comprises fat cells.

9. The method of claim 1, wherein the undesired fluid comprises cancer cells.

10. The method of claim 1, wherein the undesired fluid comprises brain cells.

11. The method of claim 1, wherein the undesired fluid comprises bacteria.

12. The method of claim 1, wherein the undesired fluid comprises artificial materials.

13. The method of claim 1, wherein the destruction of the undesired fluid comprises apoptosis.

14. The method of claim 1, wherein the undesired fluid comprises a diseased cell.

15. The method of claim 1, wherein the undesired fluid comprises 8-oxo-2'-deoxyguanine.

16. The method of claim 1, wherein the undesired fluid comprises a virus.

17. The method of claim 1, wherein the undesired fluid comprises atherosclerotic plaque.

18. The method of claim 1, wherein the undesired fluid comprises mitochondrial DNA.

19. The method of claim 1, wherein the undesired fluid comprises inflamed tissue.

20. The method of claim 1, wherein the undesired fluid comprises free radicals.

* * * * *